(12) United States Patent
Larche et al.

(10) Patent No.: US 9,452,004 B2
(45) Date of Patent: Sep. 27, 2016

(54) DEVICE FOR COMPRESSING TWO BONE PARTS

(75) Inventors: Gregoire Larche, Cholet (FR); Jean-Pierre Podgorski, Saint-Crespin-sur-Moine (FR)

(73) Assignee: D.L.P., Haute Goulaine (FR)

( * ) Notice: Subject to any disclaimer, the term of this patent is extended or adjusted under 35 U.S.C. 154(b) by 651 days.

(21) Appl. No.: 13/991,076

(22) PCT Filed: Dec. 1, 2011

(86) PCT No.: PCT/FR2011/052837
§ 371 (c)(1),
(2), (4) Date: May 31, 2013

(87) PCT Pub. No.: WO2012/072956
PCT Pub. Date: Jun. 7, 2012

(65) Prior Publication Data
US 2013/0253592 A1    Sep. 26, 2013

(30) Foreign Application Priority Data

Dec. 1, 2010    (FR) ...................... 10 59962

(51) Int. Cl.
*A61B 17/66*    (2006.01)
*A61B 17/80*    (2006.01)

(52) U.S. Cl.
CPC ................. *A61B 17/8019* (2013.01)

(58) Field of Classification Search
CPC  A61B 17/80; A61B 17/808; A61B 17/8004; A61B 17/8014; A61B 17/8019
USPC .............. 606/280–299, 70, 71, 105
See application file for complete search history.

(56) References Cited

U.S. PATENT DOCUMENTS

| 4,119,092 | A | 10/1978 | Gil |
| 2007/0276383 | A1 | 11/2007 | Rayhack |
| 2009/0228047 | A1 | 9/2009 | Derouet et al. |
| 2011/0238068 | A1 | 9/2011 | Bernsteiner |

FOREIGN PATENT DOCUMENTS

| AT | 506 937 A4 | 1/2010 |
| FR | 2 348 686 A1 | 11/1977 |
| WO | 2010/060124 A1 | 6/2010 |

OTHER PUBLICATIONS

International Search Report for PCT/FR2011/052837, mailing date of Feb. 2, 2012.

*Primary Examiner* — Kevin T Truong
*Assistant Examiner* — Si Ming Ku
(74) *Attorney, Agent, or Firm* — Westerman, Hattori, Daniels & Adrian, LLP

(57) ABSTRACT

The present invention relates to a device for moving together and compressing two bone parts, consisting of: a) a plate (2) provided with a plurality of through-openings (12, 14, 16, 17); and b) a means (3, 4) for moving said two bone parts together, including: a base (20), suitable for being attached to said plate (2), comprising at least one oblong through-opening (28), at least one of the side edges (28b) of which comprises a rack (28b'); and a control tool (4) including a head (46) provided with (i) an end rod (47) to be inserted into a hole made in said bone material and (ii) a pinion (48) for meshing with said rack (28b') of the base (20), such that rotating said head (46) about said stationary axis of rotation (4') causes the translation of said base (20) and of said associated plate (2) relative to said head (46), so as to achieve the sought action of moving together and compressing.

20 Claims, 5 Drawing Sheets

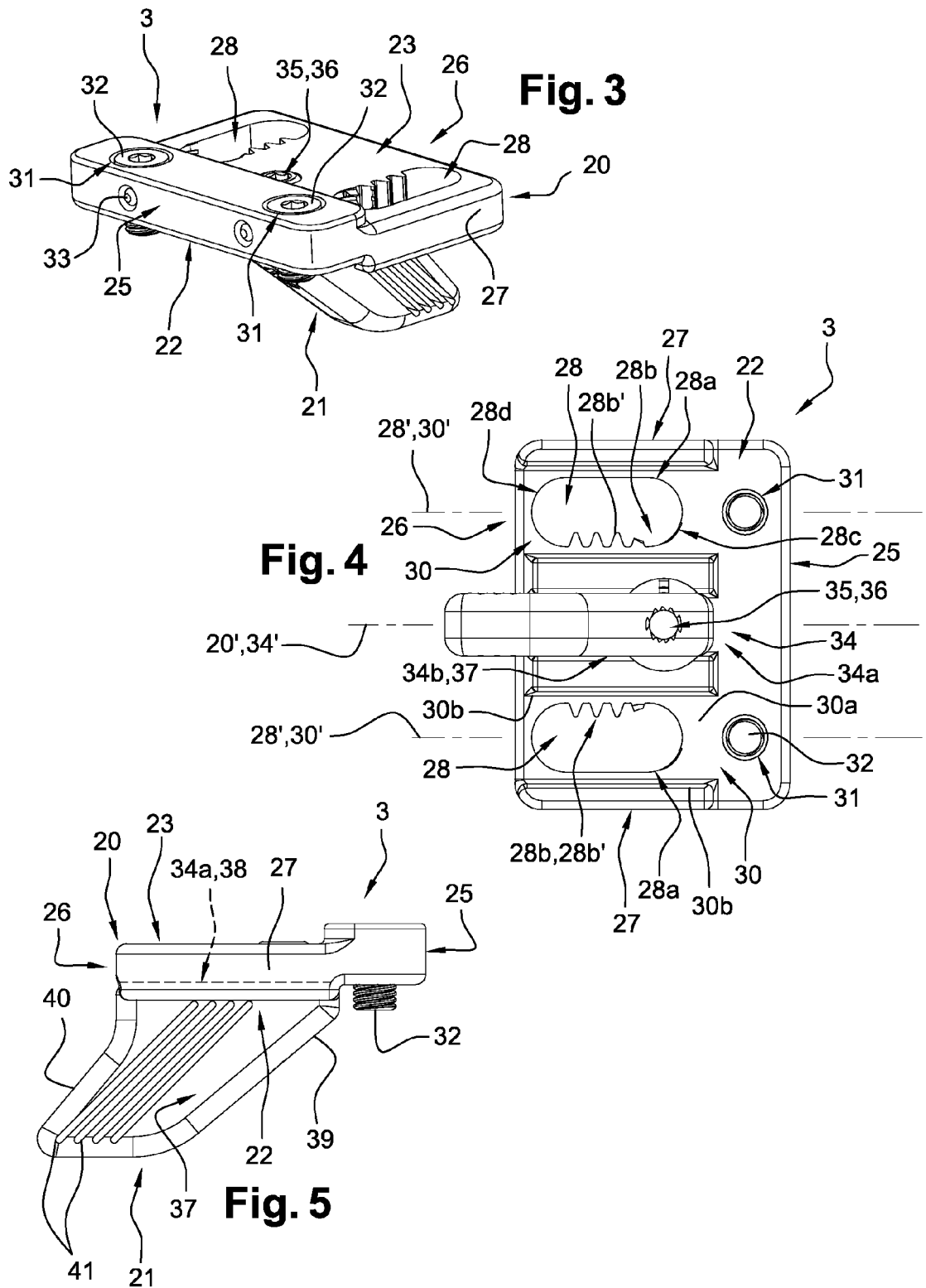

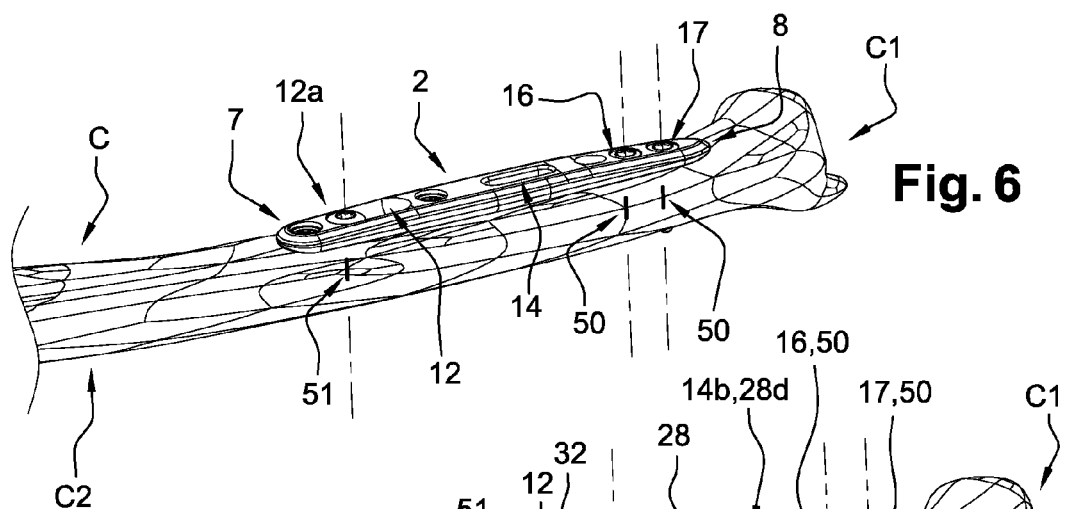
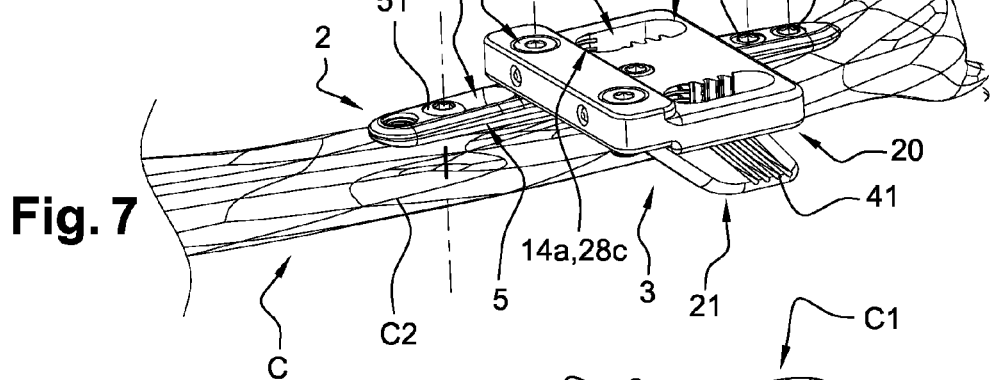
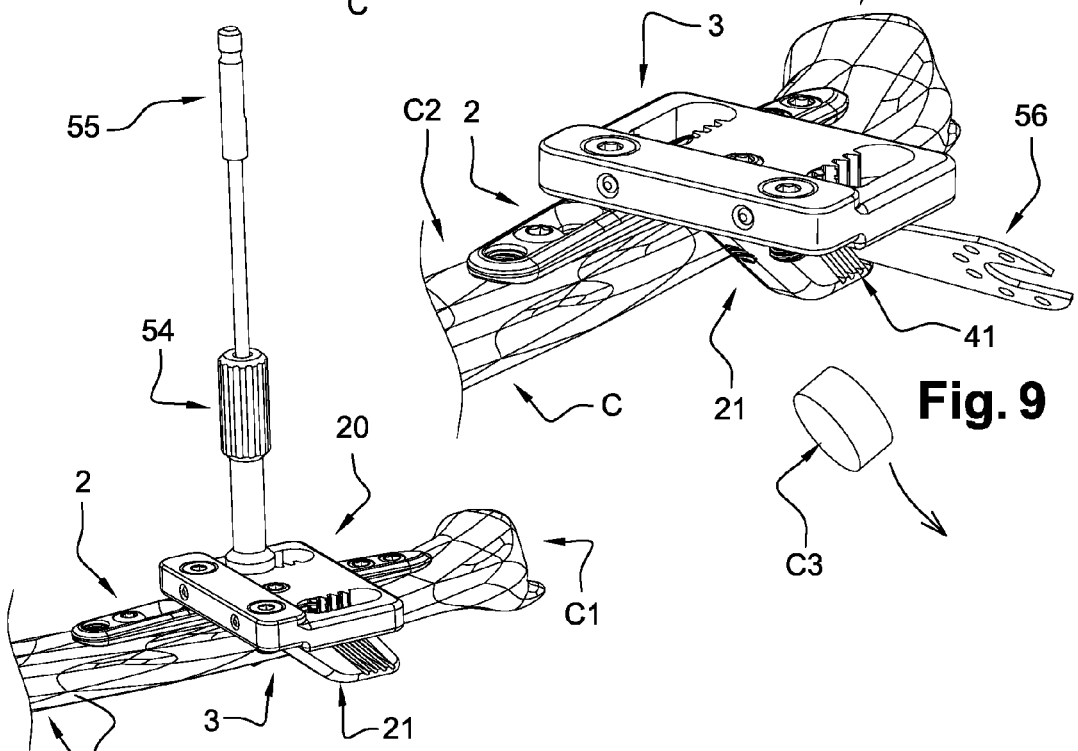

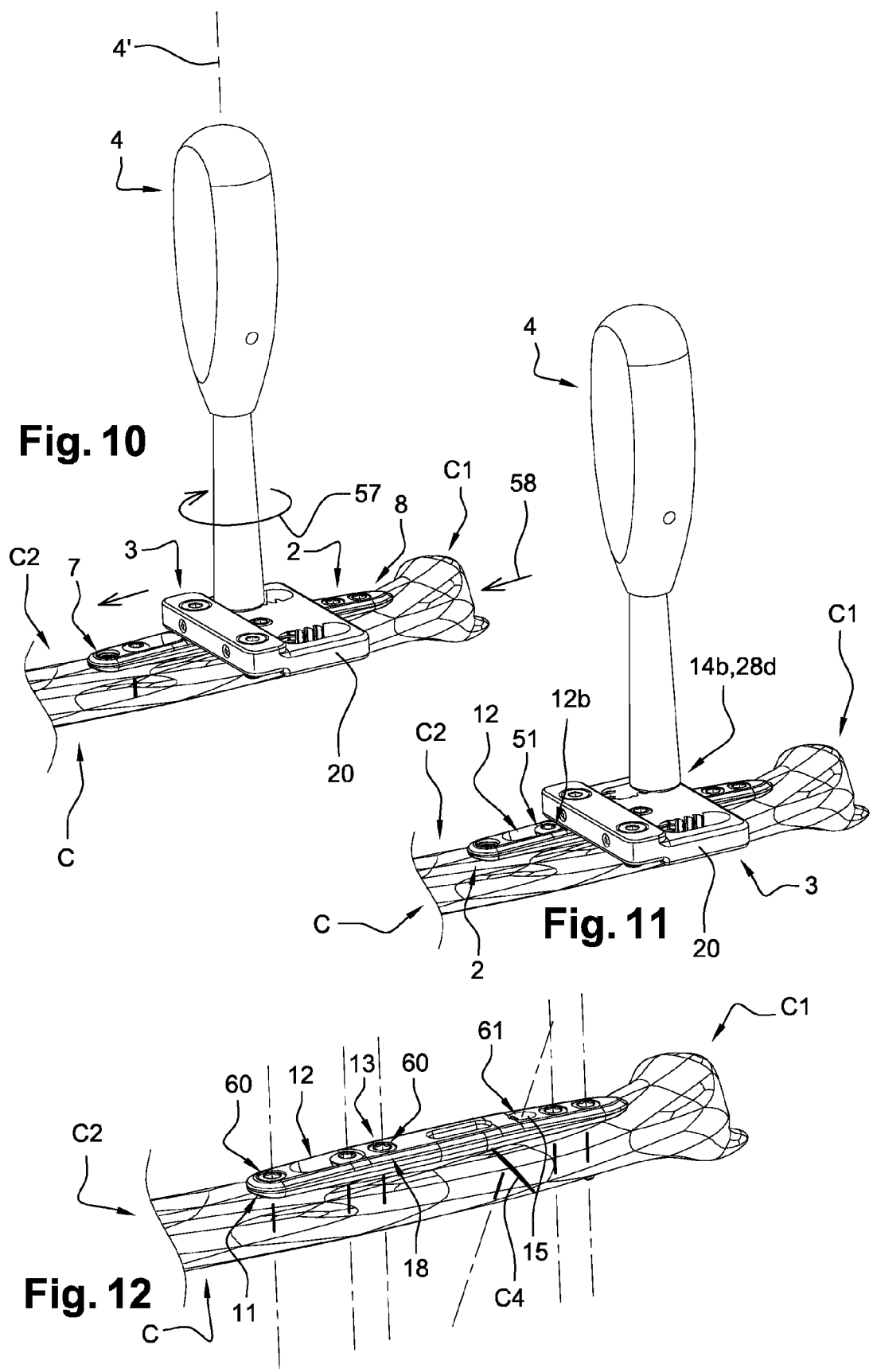

DEVICE FOR COMPRESSING TWO BONE PARTS

The present invention relates to the field of equipment used for the implementation of bone surgery techniques.

Some pathologies of the skeleton, affecting in particular the cubitus (also called "ulna") or some other long bones, are effectively treated by a bone segmental shortening technique.

For example, during osteotomy of the radius for the treatment of a malunion located at the lower end thereof, an ulnar impaction syndrome is generated, accompanied with an inferior radio-ulnar and ulno-carpal conflict, which generate pains and which pose problems of wrist mobility.

To remedy these problems, a conventional surgical treatment consists in shortening the cubitus, by making a resection of a diaphyseal ring, followed by an osteosynthesis with a plate-and-screw system loaded in tension.

Such strategy allows restoring approximate anatomy of the inferior radio-ulnar articulation, and thus efficiently remedying the pronosupination pains and troubles.

An equipment for implementing such a technique of cubitus segmental shortening is described, for example, in the document US-2007/0276383.

The corresponding equipment comprises in particular three devices intended to be fixed to the bone for the implementation of this surgical technique, i.e.:
- a device for guiding the cutting of the bone segment, comprising (i) a base for the fixation thereof directly on the bone to be shorten, and (ii) an actual guiding part, provided with slots intended to cooperate with the blade of a cutting tool;
- an osteosynthesis plate, fixed directly on the epiphyseal bone part and on the diaphyseal part, after the cutting of the bone segment and the removal of the guiding device ; and
- a compression device, intended to be temporarily mounted on the osteosynthesis plate and to cooperate with the two bone parts, so as to operate their approximation by compression.

But such an equipment is not fully satisfying.

In particular, it is necessary to remove the cutting device to add afterwards the osteosynthesis plate. During this step, the two bone parts are no longer held with respect to each other; in practice, the practitioner may then have some difficulty to suitably fix the osteosynthesis plate on the two bone parts separated from each other.

It results therefrom, in particular, problems of rotation and misalignment of these two parts, which are likely to harm their optimal approximation.

Another material for the implementation of this same technique of bone shortening, and corresponding to the preamble of claim 1, is described in the document WO-2010/060124.

The corresponding material comprises an osteosynthesis plate provided with several through-openings, in particular two end openings, one of which is oblong, between which is provided an oblong intermediate opening; and it also comprises means, added on said osteosynthesis plate, for the compression of the two bone parts, associated with cutting means. These compression means comprise a base including, on the one hand, an oblong through-opening delimited by two straight lateral edges, and on the other hand, means for fixation on the osteosynthesis plate, for the positioning of this oblong through-opening opposite the intermediate through-opening of said osteosynthesis plate.

Herein, the operation of approximating the two bone parts is performed in a relatively complex manner, by means of a holding element that is displaced within the oblong through-opening of the base by means of an operating screw.

The document FR-2 348 686 also describes another equipment with a bone compression functionality (in particular for bone fracture reduction). In this document FR-2 348 686, an osteosynthesis plate is provided with two oblong openings, one of which includes a rack structure on one of its lateral edges; and this plate is associated with an operating tool, whose head includes, centered onto a same axis, an end rod topped with a pinion.

The end rod is intended to be introduced into a hole formed in the bone, opposite the oblong opening equipped with the rack, and the associated pinion is intended to cooperate with this rack, so as to obtain the desired bone approximation (by rotational operation of the tool).

But this type of equipment requires the making of a rack structure on each osteosynthesis plate, with the ensuing additional costs. Moreover, the making of such a rack structure is not always easy and may in some cases not being optimized, because it has to take into account size constraints of the plate.

More generally, within the framework of osteosynthesis techniques, even when it is not necessary to remove a bone segment, it is essential to obtain a good loading in compression and a good adjustment of the surfaces brought into contact of two bone fragments, so as to obtain an efficient bone consolidation.

Within this context, the applicant has developed a new equipment for approximating and loading in compression two bone fragments, which has the interest to have a simple, efficient and optimized structure, while allowing a correct permanent holding of the two bone parts with respect to each other, all along the surgical osteosynthesis technique, after a bone fracture or an osteotomy.

For that purpose, as defined in claim 1, the equipment according to the invention comprises:

a/ an osteosynthesis plate including a lower face, adapted to come into contact with the external surface of the receiving bone, which is in two bone parts (or, in other words, "two fragments"), and an opposite upper face, which plate includes two ends, defining together a longitudinal axis; this plate is also provided with several through-openings, each of which opens out at the two faces thereof, i.e.:
- a first end opening, formed on the side of a first one of said ends of said plate,
- a second end opening, formed on the side of a second one of said ends of said plate, and
- an intermediate opening, formed between said two end openings, which second end opening and intermediate opening each have a generally oblong shape, whose median axis is oriented parallel, or at least approximately parallel, to said longitudinal axis of said plate, and b/ means for the compression of said two bone parts, so as to operate an approximation and loading in compression of these two bone parts, which compression means comprise a base delimited by a lower face, adapted to come into contact with said plate, and an opposite upper face, which base includes, on the one hand, at least one oblong through-opening delimited by two parallel lateral edges defining a median axis, and on the other hand, means for fixation on said plate, for the positioning of said oblong through-opening opposite said intermediate through-orifice of the plate;

and this equipment is characterized in that one of the lateral edges of the oblong through-orifice of the base includes a rack, and in that it also includes an operating tool comprising a head intended to be introduced through the opposite oblong openings of said plate and said base, which head includes, centered on a same axis, an end rod topped with a pinion, which end rod is intended to be introduced into a hole formed in said bone material underlying said opposite oblong openings, to define a fixed rotation axis of said head, and which pinion is intended to mesh with said rack, so that the rotational operation of said head about said fixed rotation axis causes a translation movement of said base, and of said associated plate, with respect to said head, so as to obtain said approximating operation between the epiphyseal and diaphyseal bone parts.

The osteosynthesis plate of the equipment according to the invention thus allows an efficient and permanent holding of the two bone parts, all along the surgical technique.

Moreover, this osteosynthesis plate serves as a receiving support for the compression means, which allows the optimal positioning thereof on the bone, while limiting the number of fixation orifices to be formed in said bone.

The corresponding equipment further allows controlling and keeping the compression applied by the surgeon.

Furthermore, the rack integrated within the base of the compression means may be used for mounting many plates, with plates of simple structure; the corresponding equipment thus allows not taking into account the size constraints of the plate to size the rake, and hence optimizing the design thereof according to the nature of the efforts to be transmitted through it.

According to another feature, the lower face of the base of the compression means is provided with at least one positioning groove intended to cover the plate, to within the clearance, which positioning groove is delimited—by an upper wall, which is intended to rest on the upper face of said plate and at which opens out the rack oblong orifice, and—by two lateral walls, each intended to come opposite one of the lateral edges of said plate to form lateral stops, which lateral walls define a longitudinal axis oriented parallel to the medial axis of the associated oblong opening.

According to still another feature of the invention, the osteosynthesis plate comprises a tapped opening that opens out at the upper face thereof, formed between the end oblong opening and the intermediate oblong opening; and the base includes at least one through-opening through which is added a screw for fixation on said plate tapped opening, which through-opening is formed on the median axis of the rack oblong opening.

Still according to the invention, the osteosynthesis plate advantageously includes an additional through-opening whose axis is inclined with respect to the faces of said plate, to allow the positioning of a compression screw intended to provide the link between the approximated bone fragments.

This characteristics allows fixing the bone consolidation focus point by means of a self-compression screw passing through it.

According to an improved embodiment, the equipment according to the invention is further adapted for the segmental shortening of a long bone (in particular the cubitus) by osteotomy of a bone segment.

For that purpose, the equipment according to the invention also comprises a lateral extension for guiding the cutting operation, adapted to be fixed (directly or indirectly) on the osteosynthesis plate so as to extend under the plane of the lower face of said plate, which extension is provided with through-slots for guiding a cutting tool, so as to allow the osteotomy of the bone segment under said plate, between the two end openings.

The compression means are then here useful for approximating and compressing said two bone parts, after osteotomy of said bone segment.

According to this embodiment, the cutting-guide lateral extension is carried by the base of the compression means to form a guiding/compression unit. This lateral extension is thus fixed on the plate through this base.

In this case, the lateral extension is advantageously fastened to the base of the compression means, through removable fixation means (for example one or several screws).

The lateral extension then advantageously consists in an added-on member that includes—two longitudinal faces, at which open out the through-slots, and—an upper face, that is fastened to the lower face of the base through a screw.

Moreover, the lower face of the base of the compression means advantageously includes a positioning groove receiving an upper part of the lateral extension, fixed by means of a single screw.

According to another characteristics, the base of the compression means advantageously includes two oblong through-openings, arranged remote and parallel relative to each other, each including a longitudinal edge provided with a rack for application of the surgical technique on a right or a left part of a patient.

In this case, each of these oblong openings is preferably associated with a positioning groove on the osteosynthesis plate; and the lateral extension is advantageously formed between these two oblong openings.

Still according to this embodiment, the lateral extension includes at least two through-slots, arranged parallel and remote relative to each other, which are oriented according to a plane inclined with respect to the faces of the plate, for a bevelled cutting of the bone segment.

For loading the two bone parts in compression, the method of implementation of the equipment according to the invention comprises at least the following successive steps:

(a) a step of fixing the osteosynthesis plate on the two bone parts to be loaded in compression, by screwing into the bone a first screw through the first end opening and a second screw through the oblong end opening, said second screw being not locked and being arranged within said oblong opening on the side of said second end of said plate, (b) a step of fixing on the plate the base of the compression means, (c) a step of drilling a hole into the bone material underlying said opposite oblong openings of said plate and said base, on the side of said second end of the plate, (d) a step of introducing the head of the operating tool through the opposite oblong openings of said plate and said base, so that the end rod thereof enters into the receiving bone hole and so that the pinion thereof meshes with the rake of the oblong opening of said base, (e) a step of rotationally operating said operating tool about its longitudinal axis, so as to cause a translation movement of said base, and of said associated plate, with respect to said head, so as to obtain said desired operation of approximation of the two bone parts, (f) a step of holding in position the operating tool about its longitudinal axis, and of locking said second screw in its oblong end opening, (g) a step of extracting said operating tool with respect to said plate and said base, (h) a step of dismounting said base, (i) if need be, a step of further fixing the two bone parts by inserting a compression screw through the inclined opening of said plate.

For the implementation of a technique of segmental shortening of a long bone, the method of implementation of the equipment according to the invention comprises at least the following successive steps:

(a') a step of fixing the osteosynthesis plate on the bone to be shortened, by screwing into the bone a first screw through the first end opening and a second screw through the oblong end opening, said second screw being not locked and being arranged within said oblong opening on the side of said second end of said plate, (b') a step of fixing on the plate cutting-guide means and the base of the compression means, (c') a step of drilling a hole into the bone material underlying said opposite oblong openings of said plate and said base, on the side of said second end of the plate, (d') a step of cutting a bone segment under said added-on plate, by means of a cutting tool cooperating with the cutting-guide means, (e') possibly, a step of dismounting said cutting-guide means, (f') a step of removing said cut bone segment, (g') a step of introducing the head of the operating tool through the opposite oblong openings of said plate and said base, so that the end rod thereof enters into the receiving bone hole and so that the pinion thereof meshes with the rake of the oblong opening of said base, (h') a step of rotationally operating said operating tool about its longitudinal axis, so as to cause a translation movement of said base, and of said associated plate, with respect to said head, so as to obtain said desired operation of approximation of the two bone parts, (i') a step of holding in position the operating tool about its longitudinal axis, and of locking said second screw in its oblong end opening, (j') a step of extracting said operating tool with respect to said plate and said base, (k') a step of dismounting said base, and, if need be, the cutting-guide means, (l') if need be, a step of further fixing the two bone parts by inserting a compression screw through the inclined opening of said plate.

The invention will be further illustrated, without being limited in any way, by the following description of a particular embodiment, given only by way of example, in relation with the appended drawings, in which:

FIG. 3 is a perspective and isolated view of the device that can be viewed in FIG. 1, added on the osteosynthesis plate for guiding the cutting of the bone segment and for the compression of the two obtained bone parts;

FIG. 4 is a bottom view of the guiding/compression device shown in FIG. 3;

FIG. 5 is a side view of the guiding/compression device according to FIGS. 3 and 4, showing the lateral extension thereof provided with through-slots for a bevelled cutting of the bone;

FIGS. 6 to 12 illustrate the main steps successively implemented for the segmental shortening of the cubitus, by implementation of the equipment shown in FIGS. 1 to 5;

Figure 1:
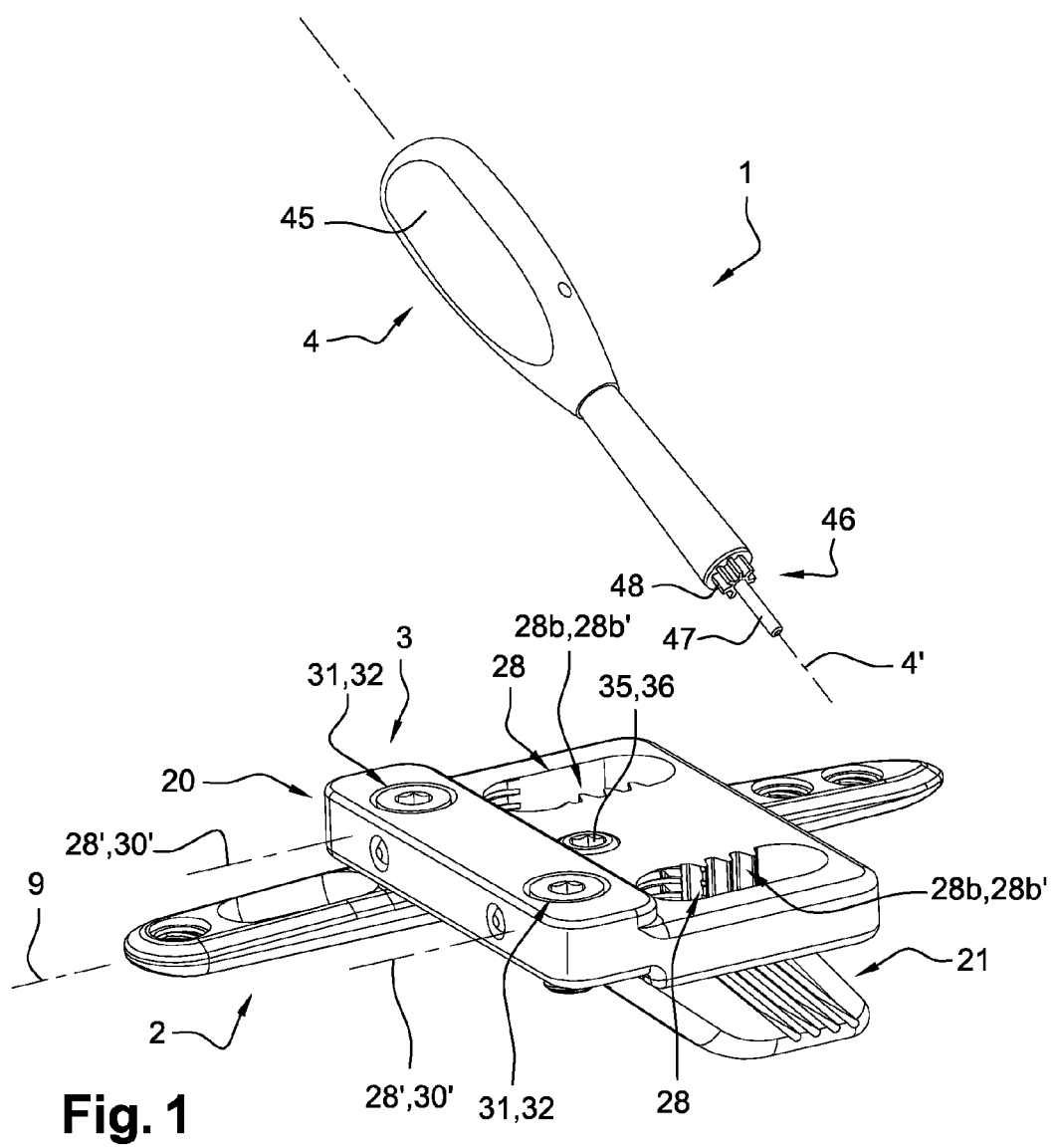
FIG. 1 is a general perspective view of the different devices constituting a possible embodiment of the surgical equipment according to the invention.

The surgical equipment 1, generally shown in perspective view in FIG. 1, consists in a set of devices (or ancillaries) that are adapted to allow the practitioner to implement a technique of segmental shortening of a long bone, and in particular a cubitus.

This equipment may be in the form of a bone surgery "kit" proposed to the surgeon.

The equipment 1 in question comprises the following devices:

(i) an osteosynthesis plate 2, intended to be fixed on the cubitus to be shortened by means of a set of screws, intervening in the segmental osteotomy of the bone and also in the subsequent osteosynthesis;

(ii) a guiding/compression device 3, intended to be fixed on said osteosynthesis plate 2 to guide the cutting of the bone segment and also to provide a loading in compression of the two thus-obtained bone parts; and (iii) an operating tool 4, intended to cooperate with the bone to be shortened and with said guiding/compression device 3, so as to generate a translation movement of the latter, and of said associated plate 2, on said bone, so as to obtain a guided approximation between said two bone parts.

In the present description, the terms "bone parts" and "bone fragments" are used as synonyms and in an equal manner.

Figure 2:
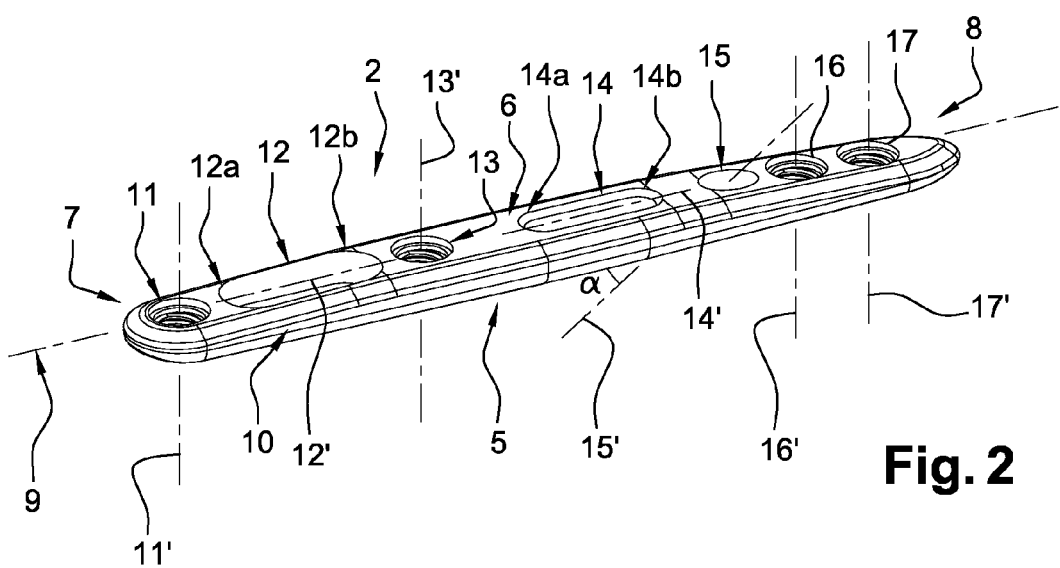
FIG. 2 is a perspective and isolated view of the osteosynthesis plate making part of the equipment according to FIG. 1.

The osteosynthesis plate 2 is illustrated in more details, and in an isolated manner, in FIG. 2.

This plate 2, in the general shape of an elongated flat small bar, includes (i) a lower face 5, adapted to come into contact with the external surface of the receiving bone (as shown in FIGS. 6 to 12), and (ii) an upper face 6, intended to come opposite the bone.

These lower 5 and upper 6 faces extend up to two ends 7 and 8, according to a longitudinal axis 9.

The plate 2 is delimited on its sides by two longitudinal edges 10 located on each side of the axis 9.

The two ends 7 and 8 are intended to be located on the side of the bone diaphysis and of the bone epiphysis, respectively.

This plate 2 is also provided with through-openings 11 to 17, which, on the one hand, each open out at the faces 5 and 6, and on the other hand, are distributed along the longitudinal axis 9.

More precisely, from the diaphyseal end 7 to the epiphyseal end 8 of the plate 2 (i.e. from left to right in FIG. 2), the openings are respectively designated by the references 11 to 17, and consist successively in:

(i) a cylindrical end opening 11, located on the side of the diaphyseal end 7, whose axis 11' extend perpendicular to the longitudinal axis 9, (ii) an oblong end opening 12, also formed on the side of said diaphyseal end 7, and whose median axis 12' is located on the longitudinal axis 9 of the plate 2, (iii) a cylindrical intermediate opening 13, whose axis 13' is oriented perpendicular to the longitudinal axis 9 of the plate 2, (iv) an oblong intermediate opening 14, whose median axis 14' is located on the longitudinal axis 9 of the plate 2, (v) a cylindrical opening 15, whose axis 15' is inclined with respect to the longitudinal axis 9, and (vi) two other cylindrical end openings 16 and 17, formed on the side of the epiphyseal end 8 of the plate 2, whose axes extend perpendicular to the axis 9.

The cylindrical openings 11, 13, 16 and 17 have tapped inner profiles intended to cooperate with complementary threads formed on the associated fixation screw bodies.

The two oblong openings 12 and 14 each include two ends, i.e. a so-called diaphyseal end 12a, 14a (located on the side of the diaphyseal bone part) and a so-called epiphyseal end 12b, 14b (located on the epiphyseal bone part), located on their respective median axes 12' and 14'. These two oblong openings 12 and 14 have advantageously the same length, comprised for example between 0.7 and 1.5 cm.

The inclined through-opening 15, here not tapped, includes an axis 15' extending along an ascending slope, in a direction oriented from the diaphyseal end 7 to the epiphyseal end 8.

This axis 15' thus defines an acute angle (α) with the longitudinal axis 9 of the plate 2, which is advantageously comprised between 30° and 50°.

The function of each of these openings 11 to 17 is detailed hereinafter in relation with FIGS. 6 to 12.

Preliminarily, the through-openings 11, 12, 13, 15, 16 and 17 of the plate 2 are each intended to receive a bone fixation screw.

The oblong intermediate opening 14 is intended to receive the operating tool 4 for the operation of approximation of the two bone parts, subsequent to the cutting of the bone segment.

The cylindrical intermediate opening 13 is also provided to receive a screw for fixation of the guiding/compression device 3.

The guiding/compression device 3 of FIG. 1 is shown in details, and in an isolated manner, in FIGS. 3 to 5.

This guiding/compression device 3 comprises:

(i) a base (20), intended to be fixed directly on the plate 2 and intended to cooperate with the operating tool 4 to form together compression means for approximating the two bone parts, and (ii) a lateral extension 21, here carried by the base 20 and intended to cooperate with a cutting tool for the osteotomy of the bone segment to be removed.

The base 20, in the general shape of a platen, is delimited (i) by a lower face 22, intended to come into contact with the plate 2, and (ii) by an opposite upper face 23.

These two faces 22 and 23 are connected (i) by two transverse edges, i.e. a so-called "diaphyseal" edge 25 and a so-called "epiphyseal" edge 26, intended to be oriented on the side of the bone diaphysis and of the bone epiphysis, respectively, and (ii) by two lateral edges 27, defining a median longitudinal axis 20'.

This base 20 also includes two rack oblong through-openings 28, which each open out at the two faces 22 and 23 of the base 20, and which are located on either side of the median axis 20'.

In practice, one of these two oblong openings 28 is intended to come opposite the oblong intermediate opening 14 of the plate 2, when the base 20 is fixed on this plate 2.

This allows proposing to the practitioner a choice of orientation of the base 20 with respect to the plate 2, as a function of whether the operation is on the right or the left arm of the patient.

These two oblong through-openings 28 are each delimited—by two parallel lateral edges 28a and 28b, defining a median axis 28' parallel to the median axis 20' of the base 20, and—by two ends 28c and 28d.

The two parallel lateral edges 28a and 28b of each opening 28 consist, respectively, in:

(i) an external lateral edge 28a, located on the side of one of the lateral edges 27 of the base 20, having a rectilinear aspect, and (ii) an internal lateral edge 28b, located remote form the lateral edges 27 of the base 20 and comprising a straight toothed rack 28b'.

The two ends 28c and 28d of each oblong through-opening 28 consist In—a so-called "diaphyseal" end 28c and—a so-called "epiphyseal" end 28d, located on the side of the diaphyseal edge 25 and of the epiphyseal edge 26, respectively, of the base 20.

At its lower face 22, the base 20 is provided with two positioning grooves 30 each adapted to cover the plate 2, to within the clearance.

The two guiding grooves 30 are each delimited by:

(i) an upper wall 30a, at which opens out one of the rack oblong openings 28 and which is intended to rest on the upper face 6 of the plate 2, and (ii) two side walls 30b, arranged parallel relative to each other, and relative to the median axis 28' of the associated opening 28, and which are each intended to come opposite one of the lateral edges 10 of the plate 2 to form lateral positioning stops.

The two lateral walls 30b of each guiding groove 30 define a longitudinal axis 30' that is merged with the median axis 28' of the associated oblong opening 28.

On the side of its diaphyseal edge 26, the base 20 also comprises means for its fixation on the plate 2.

The corresponding fixation means comprise two through-openings 31, each positioned on the median axis 28' of one of the rack oblong openings 28.

These two through-openings 31 each receive a screw 32 intended to cooperate with the cylindrical intermediate opening 13 of the osteosynthesis plate 2.

These fixation screws 32 are here locked in extraction within their respective through-openings 31, by a pin 33 going out at the diaphyseal edge 25 of the base 20.

At the median axis 20', the lower face 22 of the base 20 also includes a central groove 34 sized in such a manner to receive the upper part of the lateral extension 21.

This receiving groove 34 is delimited (i) by an upper wall 34a and (ii) by two lateral walls 34b, formed opposite to each other and parallel to the lateral edges 27 of the base 20.

This receiving groove 34 thus comprises a longitudinal axis 34' that is merged with the median axis 20' of the base 20.

The lateral extension 21 is thus carried by the base 20, extending perpendicular from its lower face 22 and arranged between the two rack oblong openings 28.

This lateral extension 21 is fastened to the base 20, through removable fixation means 35 and 36.

Here, the base 20 includes for that purpose a cylindrical through-opening 35 receiving a screw 36 cooperating with the lateral extension 21. This through-opening 35 is formed on the median axis 20' of the base 20; it is arranged in such a manner to open out, at its upper face 23 and lower face 22, in the upper wall 34a of the groove 34.

The lateral extension 21 consists in an added-on member, generally parallelepiped in shape, that includes:

(i) two longitudinal faces 37, oriented parallel to the median axis 20' of the base 20 and resting, at their upper parts, on the lateral walls 34b of the receiving groove 34, (ii) an upper face 38, resting on the upper wall 34a of the receiving groove 34, (iii) a "diaphyseal" face 39, located on the side of the diaphyseal edge 25 of the base 20, and (iv) an "epiphyseal" face 40, located on the side of the epiphyseal edge 26 of the base 20.

This lateral extension 21 is provided with several through-slots 41, arranged parallel and remote relative to each other.

These through-slots 41 open out on either side of the lateral extension 21, at the longitudinal faces 37. They are here rectilinear, and each oriented following a plane inclined with respect to the faces 5 and 6 of the base 20.

Here, these through-slots 41 each define a plane that has an ascending slope, in a direction oriented from the diaphyseal edge 26 to the epiphyseal edge 25 of the base 20. They are adapted, in position and in length, to allow the practitioner to perform a bevelled cutting of the bone, for the removal of a ring-shaped bone segment.

The operating tool 4, shown in FIG. 1, comprises a handle 45 and an operating head 46, having together a longitudinal axis 4'.

This head 46 includes, centered on the longitudinal axis 4', an end rod 47 topped with a pinion 48.

The end rod 47 has a generally cylindrical shape; its length may be of the order of 15 to 25 mm, preferably of the order of 20 mm, and its diameter is of the order of 2 to 3 mm, preferably of the order of 2,5 mm.

The pinion 48 includes a spur toothing on its periphery; its axis is centered on the longitudinal axis 4'.

The head 46 of the tool is intended to be introduced through superimposed oblong openings 14 and 28 opposite the assembled plate 2 and base 20.

More precisely, as developed hereinafter in relation with FIGS. 6 to 12, the end rod 47 is intended to be introduced through the intermediate oblong opening 14, and to enter into a hole previously formed in the bone material, opposite the superimposed oblong openings 14 and 28; the pinion 48 is intended to come within the space of the oblong opening 28 and to mesh with its rack 28b'.

The equipment 1 according to the invention also includes the different screws described hereinafter, which are intended to cooperate with the plate 2 for its fastening to the bone material.

A surgical process of segmental shortening is described hereinafter in relation with FIGS. 6 to 12, for a cubitus C, an epiphyseal part C1 and a diaphyseal part C2 of which are shown.

This surgical process begins, after preparation of the operative field, by a suitable orientation and positioning on the plate 2 on the cubitus C. In particular, the diaphyseal 7 and epiphyseal 8 ends of the plate 2 are placed on the side of the diaphysis C2 and epiphysis C1 parts of the cubitus C, respectively.

Two first mono-axial screws 50 (shown very schematically by a thick line in FIG. 6) are added on and locked through the two epiphyseal end openings 16 and 17 of the plate 2.

A third compression screw 51 (also illustrated very schematically in FIG. 6 by a thick line) is then introduced through the oblong end opening 12, on the side of its diaphyseal end 12a.

This third screw 51 is not locked, i.e. it is added on in such a manner not to be fully compressed. As described hereinafter, this assembly will allow the subsequent translation of the plate 2 on the bone and along this third screw 51 and guided by this latter.

On the other hand, the guiding/compression device 3 is prepared for being implanted on the plate 2 added on the bone C.

A lateral extension 21 is chosen as a function of the desired cut, and suitably fixed on the base 20 by means of a screw 36.

The obtained guiding/compression device 3 may then be fixed on the plate 2, as illustrated in FIG. 7.

More precisely, the guiding/compression device 3 is added on in such a manner that (i) one of its two guiding grooves 30 covers the plate 2 and (ii) the associated rack oblong opening 28 extends above the oblong intermediate opening 14 of the plate 2.

In this case, the overlying rack oblong opening 28 of the plate 2 extends opposite the oblong intermediate opening 14, with their diaphyseal 14a, 28c and diaphyseal 14b, 28d ends, respectively opposite to each other.

The base 20 of this guiding/compression device 3 is then locked in position on the plate 2 by screwing the fixation screw 32 in the cylindrical intermediate opening 13.

The lateral extension 21 is thus arranged on one of the sides of the cubitus C, with the through-slots 41 extending opposite the bone C and under the plane of the lower face 5 of the plate 2.

A hole is then formed in the cubitus C, opposite the superimposed oblong openings 14 and 28, to receive the end rod 47 of the operating tool 4. For that purpose, as illustrated in FIG. 8, a guide 54 is first positioned through the superimposed oblong openings 14 and 28, on the side of their diaphyseal end 14a, 28c; and a drill bushing 55 is then introduced through this guide 54, to make the desired receiving hole on the side of said diaphyseal ends 14a, 28c.

The cubitus C may then be subjected to a cutting operation (FIG. 9).

For that purpose, a wobble saw is introduced successively through two through-slots 41 of the lateral extension 21, to successively make (i) a cutting line by leaning on the distal edge of a first origin slot, and (ii) a second cutting line by leaning on the proximal edge of a through-slot 41 indicating the osteotomy correction.

The osteotomy of the bone segment C3 is thus made under the plate 2 in position, i.e. opposite the lower face thereof 5, between the epiphyseal end openings 16, 17, and the diaphyseal end openings 11, 12.

The cut segment C3 may then be removed. Two separated bone parts are obtained, an epiphyseal bone part C1 and a diaphyseal bone part C2, which remain held together by the plate 2.

The removal of the bone segment C3 is facilitated by the previous dismounting of the lateral extension 21 (as illustrated by FIG. 10).

To bring back the epiphyseal part C1 in contact with the diaphyseal part C2, the practitioner first adds on the head 46 of the operating tool 4 through the superimposed oblong openings 14 and 28 (FIG. 10).

More precisely, the operator introduces the head 46 on the side of the diaphyseal end 14a, 28c of these two superimposed oblong openings 14, 28. The end rod 47 of the tool 4 then enters within the hole (not shown in the Figures), previously formed by means of the guide 54/drill bushing 55 unit.

During this positioning, the pinion 48 of the operating tool 4 is positioned through the oblong opening 28 of the base 20, to cooperate with the rack 28b' thereof.

The thus-positioned operating tool 4 is guided in rotation about a fixed rotation axis that is merged with the longitudinal axis 4' of the tool 4.

The practitioner may then begin to operate the tool 4 about its fixed axis 4', as illustrated by the arrow 57 shown in FIG. 10.

During this operation, the end rod 47 pivots within its receiving hole, and the pinion 48 meshes with the rack 28b'.

This action causes a relative translation movement of the base 20, and of the associated plate 2, both with respect to the diaphyseal part C2 and with respect to the head 46 of the operating tool 4.

The oblong end opening 12 then travels with respect to the third screw 51 fixed in the bone C, so that its epiphyseal end 12b moves closer to said screw 51 (FIG. 11). This screw 51 serves as a guide for the displacement of the plate 2 on the diaphyseal part C2.

Likewise, the superimposed oblong holes 14, 28 move in such a manner that the head 46 of the tool 4 moves closer to their epiphyseal end 14b, 28d (also FIG. 11).

The plate 2, fixed on the epiphyseal part C1 by the two first screws 50, then exerts a compression on this part C1 of the bone C, which then also undergoes a translation movement toward the diaphyseal part C2, illustrated by the arrow 58 on FIG. 10 (from right to left).

The head 46 of the tool 4 and the third screw 51, remote from each other and each cooperating with an oblong opening 28 and 12, provide together a perfect guiding in translation of the plate 2 along its longitudinal axis 9, and thus of the two bone parts C1 and C2 with respect to each other.

Once the closure of the osteotomy made (FIG. 11), the operating tool 4 is held by the practitioner to preserve the compression applied between the two bone parts C1 and C2. In the same time, the third screw 51 (mounted in the oblong end opening 12) is locked to fix the applied compression.

The base 20 of the guiding/compression device 3 is then removed (FIG. 12).

Two fixation screws 60 are added on the plate 2, on either side of the oblong end opening 12, for its fastening on the diaphyseal part C2, i.e. through the diaphyseal cylindrical end opening 11 and the cylindrical intermediate opening 13.

It is finally possible to consolidate the holding of the osteotomy focus point by inserting a self-drilling self-compression screw 61 through the inclined cylindrical opening 15.

This screw 61 is inserted according to an axis intersecting the plane C4 of the ends in compression of the two bone parts C1 and C2.

It is understood that the osteotomy technique implemented by means of the equipment 1 according to the invention has for interest to provide an optimal and permanent holding of the two bone parts C1 and C2, all along the surgical technique but also post-operation.

The two bone parts C1 and C2 are then arranged in an optimal manner during their approximation, which improves the bone regeneration and avoids (or at least limits) the offset between the two joined parts.

Moreover, a fixation of the plate on the bone parts after the osteotomy process, with the difficulties related to the holding of the parts between each other during introduction of the screws, is avoided.

This technique allows a gain of operative time and the correction performed is precise.

Figure 13:
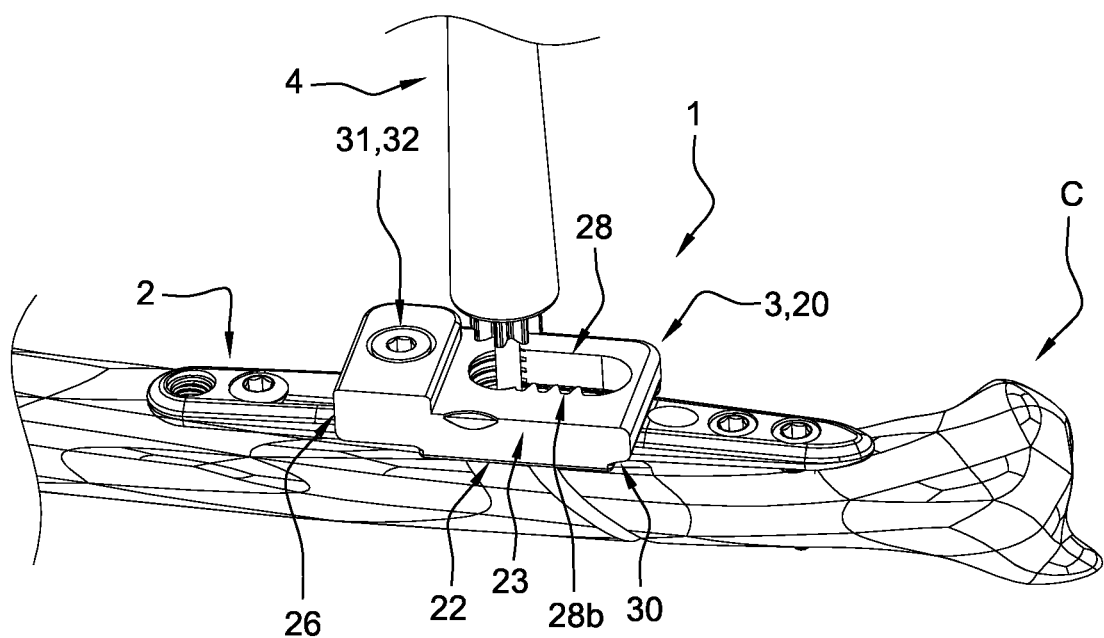
FIG. 13 is a general perspective view of a variant of the surgical equipment according to the invention, adapted for approximating and loading in compression two bone parts, without osteotomy (for example, for the treatment of a fracture).

The surgical equipment 1, generally shown in perspective view in FIG. 13, in association with a bone C, consists of a set of devices (or ancillaries) that are adapted to allow the practitioner to implement an osteosynthesis technique, and more precisely to load in compression the two bone parts, without practicing an osteotomy.

Such an equipment may for example be used for the loading in compression of two bone fragments, within the framework of treatment of a bone fracture.

This equipment is similar to that described hereinabove in relation with FIGS. 1 to 12. To facilitate the description thereof, the numerical references previously used are kept to designate the identical or similar structures.

Again, this equipment may be in the form of a bone surgery "kit" proposed to the practitioner.

The equipment 1 in question comprises the following devices:

(i) an osteosynthesis plate 2, intended to be fixed on the bone parts to be loaded in compression, by means of a set of screws, intervening in the loading in compression and also in the subsequent osteosynthesis;

(ii) a compression device 3, intended to be fixed on the osteosynthesis plate 2 to ensure the loading in compression of the two bone parts; and (iii) an operating tool 4 (partially shown here), intended to cooperate with the bone and with the compression device 3, so as to generate a translation movement of the latter, and of said associated plate 2, on said bone, so as to obtain a guided approximation between said two bone parts.

The osteosynthesis plate 2 and the operating tool 4 are here identical to those described hereinabove in relation with FIGS. 1 to 12.

This equipment is distinct from that which has been described above by the structure of its compression device that corresponds as a whole to a half of the above-described guiding/compression device 3.

More precisely, this compression device 3 comprises the base 20, intended to be fixed directly on the plate 2 and intended to cooperate with the operating tool 4 to form together means for compressing the two bone parts.

The base 20 is here again in the general shape of a platen, whose width is slightly higher than the width of the associated plate 2.

This base 20 here includes a single oblong through-opening 28 with a rack 28b, that opens out at its two faces 22 and 23.

This oblong opening 28 is intended to come opposite the oblong intermediate opening (not shown here) of the plate 2, when the base 20 is fixed on this plate 2 (FIG. 13).

At its lower face 22, the base 20 is also provided with the positioning groove 30 adapted to cover the plate 2, to within the clearance, and in which opens out the rack oblong opening 28.

On the side of its diaphyseal edge 26, the base 20 also comprises the means for its fixation to the plate 2.

The corresponding fixation means still comprise a through-opening 31, positioned on the median axis 28' of the rack oblong orifice 28, and receiving the screw 32 intended to cooperate with the cylindrical intermediate opening (not shown) of the osteosynthesis plate 2.

The surgical process of loading in compression by means of this second equipment consists in reproducing the steps described hereinabove in relation with FIGS. 6 to 12, except the steps relating to the cutting and removal of the bone segment.

Generally, the surgical techniques implemented by means of the equipment 1 according to the invention have the interest that they provide an optimal and permanent holding of two bone parts C1 and C2, all along the surgical technique but also post-operation.

The two bone parts C1 and C2 are arranged and loaded in compression in an optimal manner during their approximation, which improves the bone regeneration/consolidation and avoids (or at least limits) the offset between the two joined parts.

The invention claimed is:

1. An equipment for loading in compression of two bone parts of a long bone, in particular a cubitus, wherein said equipment comprises:
   a) a plate having a lower face, adapted to come into contact with an external surface of a receiving bone, and an opposite upper face,
   wherein said plate includes two ends, defining a longitudinal axis, and
   wherein said plate is provided with a plurality of through-openings,
   wherein each of said plurality of through-openings opens out at said lower face and upper face of the plate, and wherein said through-openings include:
   a first end opening, formed on a side of a first of said two ends of said plate,
   a second end opening, formed on a side of a second of said two ends of said plate, and
   an intermediate opening, formed between said two end openings,
   wherein said second end opening and said intermediate opening each have a generally oblong shape,
   wherein a median axis of said second end opening and a median axis of said intermediate opening are oriented at least approximately parallel to said longitudinal axis of said plate, and
   b) means for the compression of said two bone parts, so as to operate an approximation and loading in compression of said two bone parts,
   wherein said compression means comprise a base delimited by a lower base face, adapted to come into contact with said plate, and an opposite upper base face,
   wherein said base includes (i) at least one oblong through-opening delimited by two parallel lateral edges defining a median axis, and (ii) means for fixation to said plate, providing a positioning of said oblong through-opening opposite said intermediate opening of the plate,
   wherein one of said lateral edges of said oblong through-opening of the base includes a rack, and said equipment further includes an operating tool comprising a head that is to be introduced through the oblong through-opening and said intermediate opening opposite said plate and said base,
   wherein said head includes an end rod that is centered on an axis of the head and that is topped with a pinion, which end rod is to be introduced into a hole formed in a bone material underlying said opposite oblong through-opening and said intermediate opening, to define a fixed rotation axis of said head, and
   wherein said pinion is to mesh with said rack, so that a rotational operation of said head about said fixed rotation axis causes a translation movement of said base, and of said associated plate, with respect to said head, so as to obtain said operation of approximating said two bone parts.

2. The equipment according to claim 1, wherein the lower face of the base of the compression means is provided with at least one positioning groove intended to cover the plate, to within a clearance, wherein the positioning groove is delimited
   by an upper wall intended to rest on the upper face of said plate and in which the oblong through-opening of the rack opens out, and
   by two lateral walls, each intended to come opposite one of a plurality of lateral edges of said plate to form lateral stops, wherein said lateral walls define a longitudinal axis oriented parallel to the median axis of the associated oblong through-opening.

3. The equipment according to claim 1, wherein the plate comprises a tapped opening that opens out at the upper face thereof, formed between the oblong second end opening and the oblong intermediate opening,
   wherein the base includes at least one base through-opening through which a screw is added for fixation onto said tapped opening of the plate, and
   wherein said base through-opening is formed on the median axis of the oblong through-opening of the rack.

4. The equipment according to claim 1, wherein the plate further includes an additional through-opening which defines an axis inclined with respect to the lower face and the upper face of said plate, to allow a positioning of a compression screw intended to provide a link between the two approximated bone parts.

5. The equipment according to claim 1, for a segmental shortening of a long bone by osteotomy of a bone segment, wherein said equipment further comprises a lateral extension for guiding a cutting of the bone segment,
   wherein the lateral extension is adapted to be fixed on the plate so as to extend under a plane of the lower face of said plate, and
   wherein said lateral extension is provided with through-slots for guiding a cutting tool, so as to allow said osteotomy of said bone segment under said plate, between said first end opening and said second end opening.

6. The equipment according to claim 5, wherein the lateral extension is carried by the base of the compression means.

7. The equipment according to claim 6, wherein the lateral extension is fastened, through removable fixation means, with the base of the compression means.

8. The equipment according to claim 7, wherein the lateral extension comprises an added-on member that includes
   two longitudinal faces, wherein the through-slots open out at said longitudinal faces, and
   an upper face, wherein said upper face is fastened to the lower face of said base by means of a screw.

9. The equipment according to claim 8, wherein the lower face of the base of the compression means includes a positioning groove receiving an upper part of the lateral extension, wherein said base and said lateral extension are fixed to each other by a single screw.

10. The equipment according to claim 5, wherein the base of the compression means comprises two oblong through-openings, arranged remote and parallel relative to each other, each including a longitudinal edge provided with a rack, and the lateral extension is arranged between the two oblong through-openings of the base of the compression means.

11. The equipment according to claim 5, wherein the lateral extension includes at least two through-slots, arranged parallel and remote relative to each other, and
    wherein said through-slots are oriented according to a plane inclined with respect to the lower face and the upper face of the plate.

12. The equipment according claim 5, which is for the segmental shortening of the cubitus.

13. The equipment according to claim 2, wherein the plate comprises a tapped opening that opens out at the upper face thereof, formed between the oblong second end opening and the oblong intermediate opening, and wherein the base includes at least one base through-opening through which a screw is added for fixation onto said tapped opening of the plate, and wherein said base through-opening is formed on the median axis of the oblong through-opening of the rack.

14. The equipment according to claim 2, wherein the plate further includes an additional through-opening which defines an axis inclined with respect to the lower face and the upper face of said plate, to allow positioning of a compression screw intended to provide a link between the two approximated bone parts.

15. The equipment according to claim 3, wherein the plate further includes an additional through-opening which defines an axis inclined with respect to the lower face and the upper face of said plate, to allow a positioning of a compression screw intended to provide a link between the two approximated bone parts.

16. The equipment according to claim 13, wherein the plate further includes an additional through-opening which defines an axis inclined with respect to the lower face and the upper face of said plate, to allow a positioning of a compression screw intended to provide a link between the two approximated bone parts.

17. The equipment according to claim 2, for a segmental shortening of a long bone by osteotomy of a bone segment, wherein said equipment further comprises a lateral extension for guiding a cutting of the segment, wherein said lateral extension is adapted to be fixed on the plate so as to extend under a plane of the lower face of said plate, and wherein said lateral extension is provided with through-slots for guiding a cutting tool, so as to allow said osteotomy of said bone segment under said plate, between said first end opening and said second end opening.

18. The equipment according to claim 3, for a segmental shortening of a long bone by osteotomy of a bone segment, wherein said equipment further comprises a lateral extension for guiding a cutting of the bone segment, wherein said lateral extension is adapted to be fixed on the plate so as to extend under a plane of the lower face of said plate, and wherein said lateral extension is provided with through-slots for guiding a cutting tool, so as to allow said osteotomy of said bone segment under said plate, between said first end opening and said second end opening.

19. The equipment according to claim 4, for a segmental shortening of a long bone by osteotomy of a bone segment, wherein said equipment further comprises a lateral extension for guiding a cutting of the bone segment, wherein said lateral extension is adapted to be fixed on the plate so as to extend under a plane of the lower face of said plate, and wherein said lateral extension is provided with through-slots for guiding a cutting tool, so as to allow said osteotomy of said bone segment under said plate, between said first end opening and said second end opening.

20. The equipment according to claim 13, for a segmental shortening of a long bone by osteotomy of a bone segment, wherein said equipment further comprises a lateral extension for guiding a cutting of the bone segment, wherein said lateral extension is adapted to be fixed on the plate so as to extend under a plane of the lower face of said plate, and wherein said lateral extension is provided with through-slots for guiding a cutting tool, so as to allow said osteotomy of said bone segment under said plate, between said first end opening and said second end opening.

* * * * *